United States Patent

Messere et al.

[11] Patent Number: 5,977,205
[45] Date of Patent: Nov. 2, 1999

[54] COMPOSITION FOR ARTIFICIAL FINGERNAILS

[75] Inventors: Mary Ann D. Messere, Conshohocken, Pa.; Robert K. Busscher, Grayslake, Ill.

[73] Assignee: Mary Ann D. Messere, Conshohocken, Pa.

[21] Appl. No.: 09/034,048

[22] Filed: Mar. 2, 1998

[51] Int. Cl.⁶ .............................. A45D 31/00; C08L 55/02
[52] U.S. Cl. ........................... 523/113; 523/105; 424/61; 524/23; 132/73
[58] Field of Search ............................... 524/23; 523/105, 523/113; 132/73; 424/61

[56] References Cited

U.S. PATENT DOCUMENTS

| | | |
|---|---|---|
| 2,887,116 | 5/1959 | Wooding . |
| 2,979,061 | 4/1961 | Greenman et al. . |
| 3,552,401 | 1/1971 | Michaelson et al. . |
| 4,222,399 | 9/1980 | Ionescu . |
| 4,646,765 | 3/1987 | Cooper et al. . |
| 4,751,935 | 6/1988 | Mast et al. . |
| 5,219,645 | 6/1993 | Schoon . |
| 5,424,342 | 6/1995 | Hashimoto ................................ 524/23 |
| 5,513,664 | 5/1996 | Krupsky . |

FOREIGN PATENT DOCUMENTS

| | | | |
|---|---|---|---|
| 167329 | 1/1986 | European Pat. Off. .................. | 132/73 |
| 4335527 | 2/1994 | Germany . | |
| 154765 | 6/1988 | Japan ....................................... | 524/23 |

*Primary Examiner*—David Buttner
*Attorney, Agent, or Firm*—William H. Eilberg

[57] ABSTRACT

A composition of matter, for making artificial fingernails, includes a mixture of protein and plastic. The preferred form of protein is gelatin. The preferred plastic is a plastic having a melting temperature of 500° F. or less. In a preferred embodiment, one forms a mixture containing about 2–8%. gelatin (by weight), the balance being plastic. The components are mixed together, liquefied, and injection molded to form artificial fingernails. The artificial fingernails made according to the present invention are strong but flexible. When affixed to a natural nail, they have been found to strengthen the underlying natural nail after being worn for about 2–3 weeks.

13 Claims, No Drawings ns of the present invention, from a reading of10 the following detailed description of the invention, and the appended claims.

COMPOSITION FOR ARTIFICIAL FINGERNAILS

BACKGROUND OF THE INVENTION

This invention relates to the field of cosmetics, and provides a composition of matter which can be used to make artificial fingernails.

Women have commonly worn artificial fingernails which are much longer than the maximum practical length of a natural nail. Such artificial nails are secured to an underlying natural nail with an adhesive. The artificial nail may be made in a desired color, or a colorant may be applied after the artificial nail has been adhered to the natural nail.

A major problem caused by artificial nails is that they impair the health of the underlying natural nail. After having been covered by an artificial nail for an extended period, the natural nail becomes very thin, and is prone to breakage. When one needs to remove the artificial nail, part of the natural nail may break or peel off.

An artificial nail requires periodic maintenance. As the natural nail grows, the artificial nail is pushed outward, and the space created by the growth of the natural nail must be filled in. Also, an artificial nail tends to dry out, slightly changing its appearance. It therefore often becomes necessary for a nail technician to take steps restore the artificial nail to its original appearance. Such steps may include clipping the edges of the artificial nail. If the underlying natural nail is very thin, it may break during this maintenance process. As a result, the wearer often must either make a commitment to wearing artificial nails permanently, to conceal the unsightly condition of her natural nails, or else she must wait for an entire set of natural nails to grow in.

Thus, there is a need for an artificial fingernail which, while affixed to a natural nail, does not degrade the strength or health of the natural nail.

The present invention provides a composition for use in making an artificial nail, which composition promotes the strength of the underlying natural nail. The invention also includes a method for making an artificial nail having the above-mentioned advantages.

SUMMARY OF THE INVENTION

The composition of the present invention includes protein and plastic, the protein and plastic being mixed together and formed into a shaped article having the form of an artificial fingernail. In the preferred embodiment, the composition includes about 2–10 percent protein (by weight), with the balance being plastic. In one especially preferred embodiment, the protein is gelatin, and the plastic is an acrylonitrile-butadiene-styrene (ABS) terpolymer. The protein and plastic are preferably mixed together, liquefied, and injection molded to form the artificial fingernails.

Artificial fingernails made of the composition of the present invention have not only been found not to cause damage to the underlying natural nail, but they have in fact been shown to increase the strength of the natural nail, even where the natural nail has been covered by the artificial nail for an extended period.

The present invention therefore has the primary object of providing a composition for use in making artificial fingernails.

The invention has the further object of providing an artificial fingernail which, when affixed to a natural nail, promotes the health of the natural nail.

The invention has the further object of providing an artificial fingernail which, when affixed to a natural nail, increases the strength of the underlying natural nail when the artificial nail is worn for an extended period.

The invention has the further object of providing a method of making an artificial fingernail.

The invention has the further object of facilitating the maintenance of artificial fingernails by providing an artificial nail which does not damage an underlying natural nail.

The reader skilled in the art will recognize other objects and advantages of the present invention, from a reading of the following detailed description of the invention, and the appended claims.

DETAILED DESCRIPTION OF THE INVENTION

The composition of the present invention comprises a mixture of protein and plastic. The protein and plastic are mixed together, heated so that the mixture becomes a liquid, and molded into the shape of an artificial fingernail. The composition is preferably molded by conventional injection molding techniques. The latter techniques are well known, and do not form part of the present invention.

In the preferred embodiment, the protein is gelatin, and the plastic is acrylonitrile-butadiene-styrene (ABS) terpolymer, available under the trademark Cycolac resin T-1000F, from GE Plastics, an affiliate of the General Electric Company. The invention is not limited to a particular plastic, however.

In general, the plastic used in the present invention should be of a type which can be injection molded using conventional techniques. Also, it is important that the selected plastic material have a relatively low melting point, preferably not more than about 500° F. If the melting point is too high, the plastic-protein mixture will burn, and will result in an unduly brittle product. Also, when the melting point is too high, the final product has an undesirably dark brown color, and may also have an unpleasant odor.

The preferred content of protein, in the composition of the present invention, is in the range of about 2–10% by weight. Since the balance of the composition is plastic, the content of plastic will correspondingly range from about 98% down to about 90%.

The following examples provide details of various compositions made according to the present invention.

EXAMPLE 1

A mixture was prepared comprising 96% plastic (by weight) and 4% gelatin (by weight). The plastic was the Cycolac resin described above. The gelatin was Type B gelatin, having a strength of about 130 Bloom, a viscosity of about 25 mps (millipoise), and a pH of about 5.54. The gelatin was obtained from Great Lakes Gelatin Co., of Grayslake, Ill. The plastic and gelatin were tumbled together, and were heated to a temperature sufficient to form a liquid capable of being injection molded. Cycolac resin melts in a temperature range of about 425–500° F. The mixture was processed by conventional injection molding equipment, and thereby formed into a plurality of artificial nails.

The resulting artificial nails had a cream color, and exhibited good strength. The protein appeared to be uniformly dispersed throughout the artificial nail.

EXAMPLE 2

The same materials used in Example 1 were used here, except that the present composition comprised 6% gelatin and 94% plastic, by weight. The resulting artificial fingernail had a deep cream color, and also exhibited good strength. The protein again appeared to be uniformly dispersed throughout the artificial nail.

EXAMPLE 3

The same materials used in Example 1 were used here, except that the present composition comprised 8% gelatin and 92% plastic, by weight. The resulting artificial fingernail had a light tan color, and was stronger than the product obtained in Examples 1 and 2. It also had an excellent gloss. There was a slight tendency of the protein to become concentrated in some places in the final product, so the dispersion of protein was not entirely uniform.

EXAMPLE 4

The same materials used in Example 1 were used here, except that the present composition comprised 10% gelatin and 90% plastic, by weight. The resulting artificial fingernail had a medium tan color, and had the same degree of strength shown by the product of Example 3. There was again a tendency of the protein to become concentrated in parts of the final product.

EXAMPLE 5

This Example shows the result obtained from a suboptimal amount of protein. The same materials used in Example 1 were used here, except that the present composition comprised 1% gelatin and 99% plastic, by weight. The resulting artificial fingernail had a white color, and was unduly soft. The plastic appeared to be layered.

The gelatin used in making the composition of the present invention preferably has the following characteristics. The gelatin should have a strength in the range of about 115–135 Bloom, a viscosity in the range of about 18–27 mps, a pH in the range of about 4.5–6.1, a moisture content of 12% or less, and an ash content of 1.5% or less. The type B gelatin used in the above-described examples was derived from calf hide. However, other types of gelatin could be used in the present invention, and the invention should not be deemed limited to a particular type. Also, it is possible to use gelatin having parameters outside the ranges specified above, and the invention should not be deemed limited by those stated ranges. In particular, one can use a gelatin having a strength of up to 300 Bloom. It is still possible to use gelatin which is outside of this range.

The protein used in the composition of the present invention need not be gelatin. Other protein substances could be used instead, and the invention should not be deemed limited to gelatin.

Artificial fingernails made of the composition of the present invention have been found to benefit the underlying natural nail. It has been found that, when such an artificial fingernail has been worn over a natural nail for about 2–3 weeks, the underlying natural nail becomes strengthened.

The artificial fingernails made according to the present invention are flexible yet strong. Thus, the product may be easily cut to shorter lengths without breaking. The product does not have an odor when it is being cut, filed, or buffed.

When the amount of protein in the composition of the present invention becomes as great as about 10%, the resulting product begins to have an unpleasant odor, especially during the molding and subsequent curing process. The problem of odors can be reduced or eliminated by reducing the concentration of protein to about 8% or less.

The invention can be modified in various ways, as will be apparent to those skilled in the art. The plastic or protein used can be varied. Although it is not preferred, a plastic having a melting temperature somewhat higher than 500° F. could be used, since gelatin does not begin to burn until the temperature reaches the vicinity of 1000° F. If the protein is gelatin, one is not necessarily limited to a particular form of gelatin, or to a gelatin having specific characteristics. The modifications suggested here should be deemed within the spirit and scope of the following claims.

What is claimed is:

1. A composition of matter comprising protein and plastic, the protein and plastic being mixed together and being formed into an article having a shape of an artificial fingernail, wherein the plastic is acrylonitrile-butadiene-styrene (ABS) terpolymer.

2. The composition of claim 1, wherein the composition includes about 2–10 percent (by weight) of protein, the balance being plastic.

3. The composition of claim 2, wherein the plastic has a melting temperature of not more than about 500° F.

4. The composition of claim 1, wherein the protein is gelatin.

5. The composition of claim 4, wherein the plastic has a melting temperature of not more than about 500° F.

6. The composition of claim 2, wherein the protein is gelatin.

7. A composition of matter comprising about 2–10 percent gelatin (by weight), the remainder being plastic, the gelatin and plastic being mixed together and being formed into a shaped article having the shape of an artificial fingernail, wherein the plastic is acrylonitrile-butadiene-styrene terpolymer.

8. The composition of claim 7, wherein the plastic has a melting temperature of not more than about 500° F.

9. A method of making an artificial fingernail, the method comprising the steps of:
 a) combining protein and plastic to form a mixture, and
 b) molding the mixture into an article having a shape of an artificial fingernail,
 wherein step (b) comprises the steps of liquefying the mixture and then injection molding the mixture.

10. The method of claim 9, wherein step (a) includes the step of selecting the protein to be a gelatin.

11. The method of claim 9, wherein step (a) includes the step of selecting the plastic to be a polymer resin.

12. The method of claim 9, wherein step (a) includes the step of selecting the plastic such that the plastic has a melting temperature of not more than about 500° F.

13. The method of claim 9, therein step (a) is preceded by the step of selecting the amount of protein from a range of about 2–10 percent, wherein the balance is selected to be plastic.

* * * * *